United States Patent [19]

Lauer

[11] 4,367,133
[45] Jan. 4, 1983

[54] ELECTROCHEMICAL GAS ANALYZER

[75] Inventor: Jay M. Lauer, Hacienda Height, Calif.

[73] Assignee: Comsip, Inc., South El Monte, Calif.

[21] Appl. No.: 234,705

[22] Filed: Feb. 17, 1981

Related U.S. Application Data

[63] Continuation-in-part of Ser. No. 164,567, Jul. 2, 1980, abandoned.

[51] Int. Cl.³ ............................................ G01N 27/30
[52] U.S. Cl. ............................ 204/195 P; 29/592 R; 204/25; 204/40; 204/46 R
[58] Field of Search .................. 204/195 P, 1 P, 25, 204/46 R, 109, 290 R, 290 F, 40; 428/673; 29/592

[56] References Cited

U.S. PATENT DOCUMENTS

| | | | |
|---|---|---|---|
| 1,738,828 | 12/1929 | Jackson | 428/673 X |
| 2,391,039 | 12/1945 | Schaefer | 204/40 |
| 2,927,886 | 3/1960 | Allen et al. | 204/46 X |
| 3,098,813 | 7/1963 | Beebe et al. | 204/195 P |
| 3,278,408 | 10/1966 | Leonard et al. | 204/195 P |
| 3,515,658 | 6/1970 | Amdur | 204/195 P |
| 3,886,058 | 5/1975 | Barna | 204/195 P |
| 4,077,861 | 3/1978 | Lauer | 204/195 P |
| 4,242,183 | 12/1980 | Kyriacou | 204/290 R X |

Primary Examiner—G. L. Kaplan
Attorney, Agent, or Firm—Edward J. DaRin

[57] ABSTRACT

An electrochemical cell (10) having a structural organization that permits it to operate as either a galvanic or polarographic cell. The structural organization includes an electrolyte reservoir (E) comprised of a solid-like material such as a gel to releasably hold a liquid electrolyte therein. The cathode electrode (K) is defined to be surrounded by a porous material (16) to convey the electrolyte to the cathode electrode (K) to provide the necessary wetting action with the evaporation through the liquid impermeable, gas permeable membrane (M) for the cell (10). The electrolyte reservoir is spaced below the membrane (M) and is solely conveyed by capillary action to the cathode electrode. A venting element (V) is defined for the cell container (11) to prevent internal pressure variations while preventing loss of electrolyte therethrough.

When the cell (10) functions as a polarographic cell the anode electrode (A) is defined with a very large porous area that permits the cell to be used over its life without the need for physically or electrically refurbishing it.

When the cell functions as a galvanic cell the anode electrode (A) is constructed and defined as a lead wool electrode.

41 Claims, 6 Drawing Figures

TO SENSING
CIRCUIT OF FIG. 4.

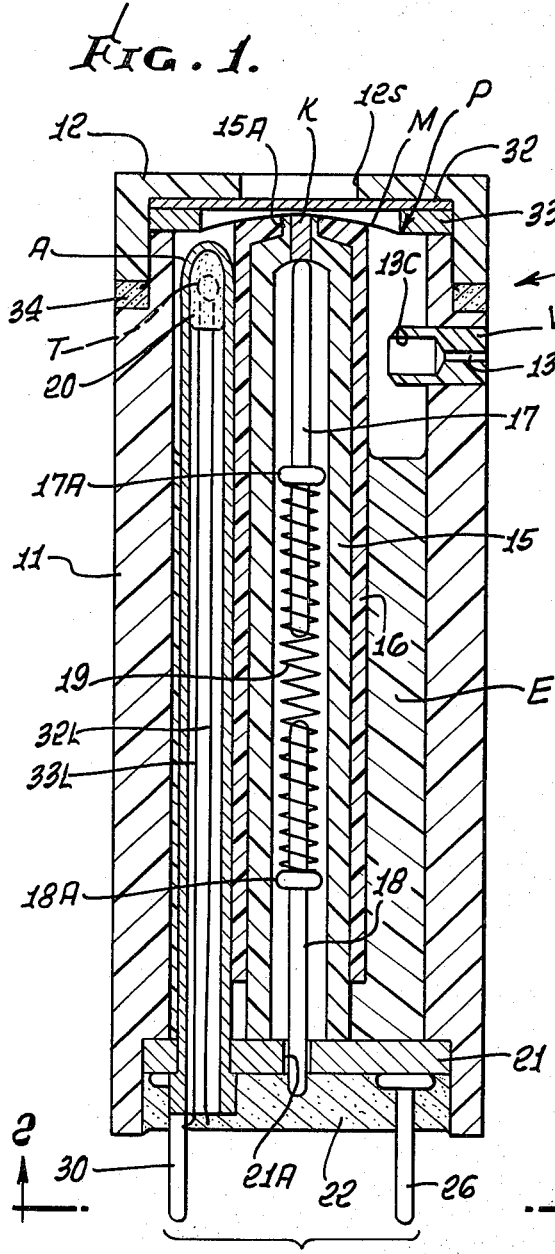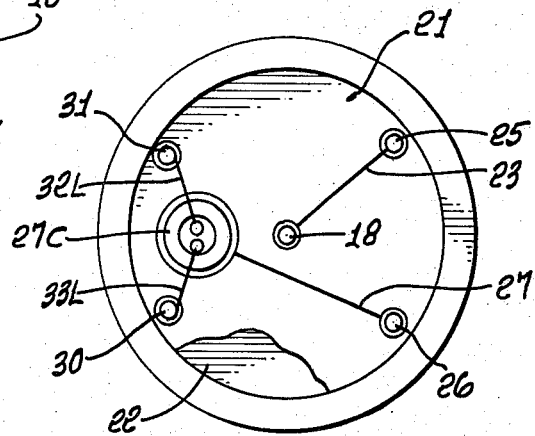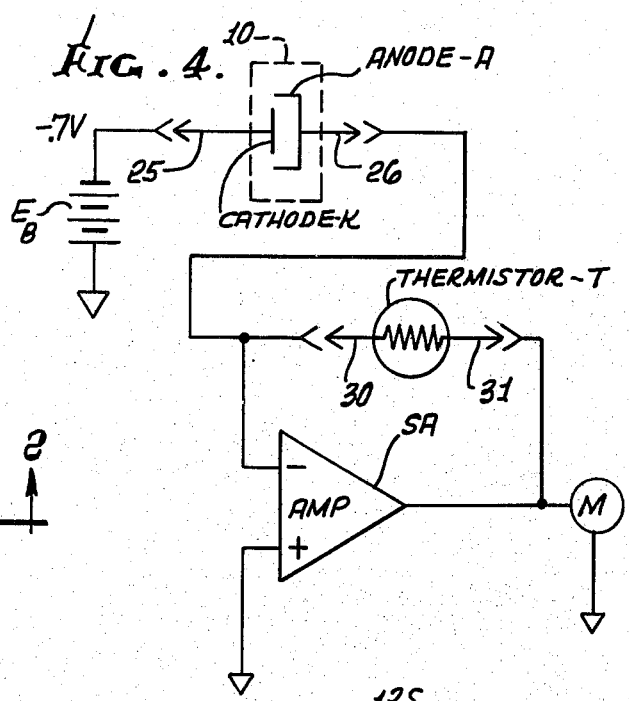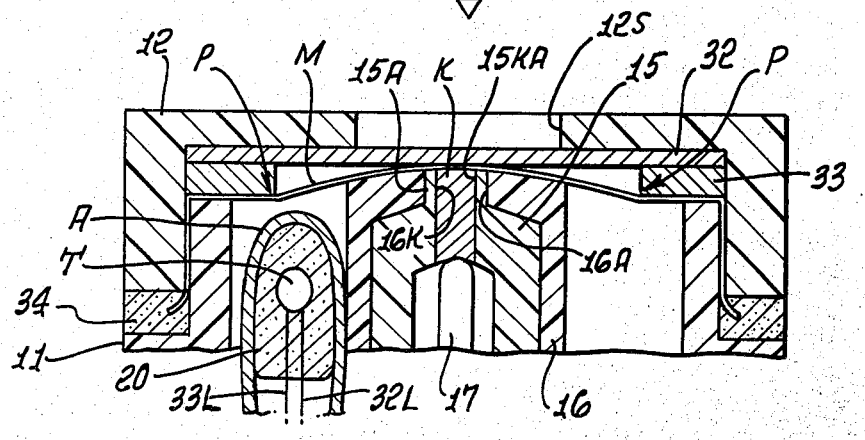

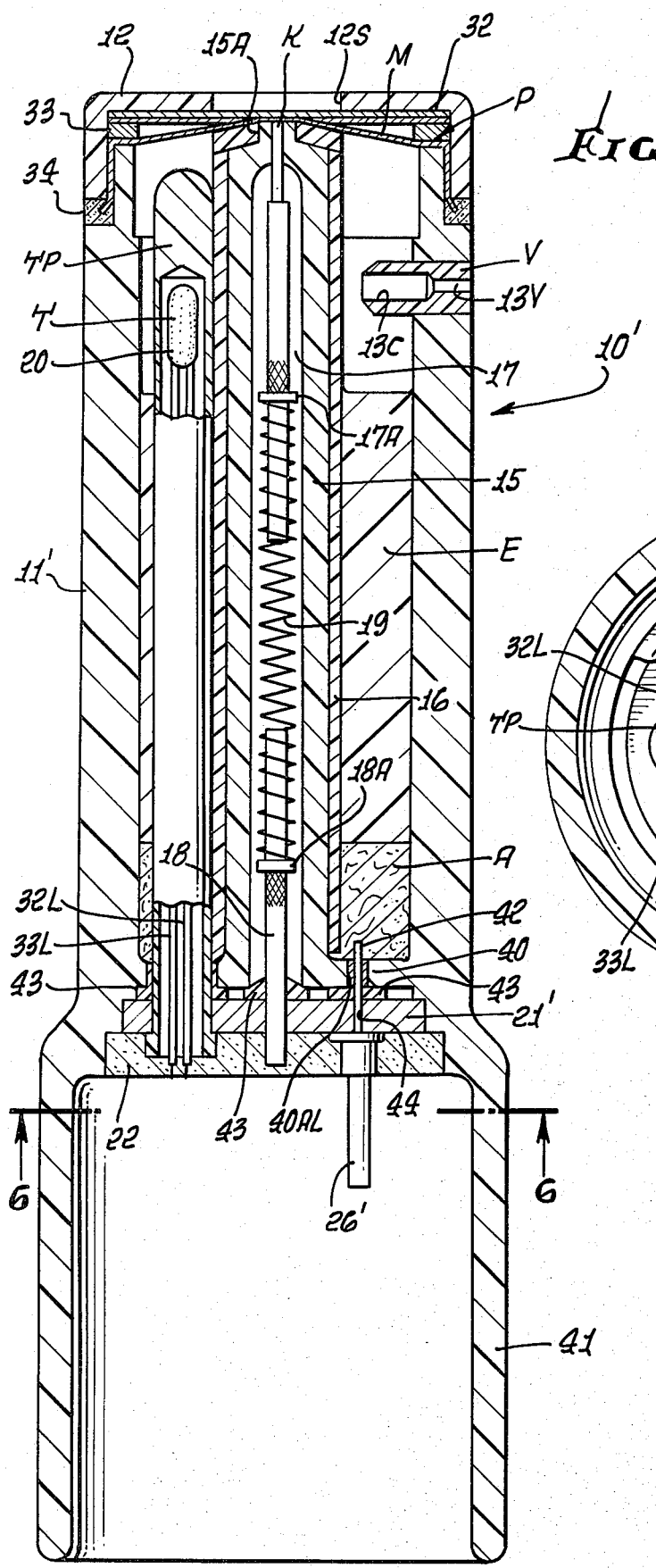
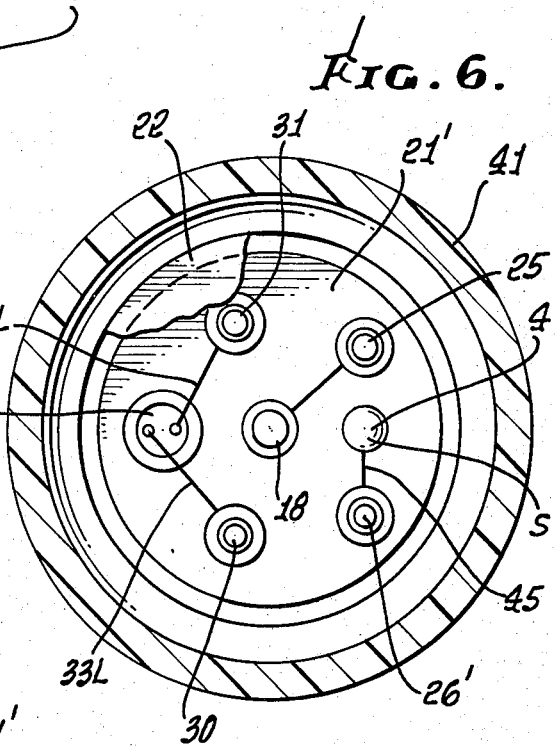

ELECTROCHEMICAL GAS ANALYZER

This application is a continuation-in-part of my co-pending application bearing Ser. No. 164,547 filed on July 2, 1980, and entitled Electrochemical Cell and assigned to the same assignee as the present application and now abandoned.

FIELD OF INVENTION

This invention relates to an electrochemical cell for electrically signalling the quantity of a gas, such as oxygen, in a gaseous mixture subjected to the cell and, in particular, to improvements in the structural organization for packaging of an electrochemical cell.

BACKGROUND OF INVENTION

Electrochemical gas analyzers as well known in the art. Typical of the gas analyzers of the prior art are disclosed in my earlier granted U.S. Pat. Nos. 3,429,796; 3,767,552, and 4,077,861. These gas analyzers are utilized as sensors for determining the oxygen concentration in a gas mixture such as air. The electrochemical cell is defined with anode and cathode electrodes for producing an electrical output signal representative of the quantity of oxygen in the sensed gas mixture. The electrochemical cells of the prior art are further characterized as either galvanic cells or polarographic cells. The galvanic cell results from choosing appropriate active anode material such as lead for causing a reaction at the cathode electrode leading to the derivation of an output current from the cell. A polarographic electrochemical cell results from the selection of silver as an anode and applying a small polarizing potential between the cathode and anode electrodes to produce the cathodic reaction. The prior art electrochemical gas analyzers are generally satisfactory, although the leakage of electrolyte from the cell has always been a problem in the prior art type of analyzers. In addition, in the polarographic type of prior art cell wherein a silver anode electrode is employed in a potassium chloride electrolyte, a portion of the silver surface will oxidize and form silver chloride and thereby coat the electrode with the insoluble silver chloride. This coating on the anode electrode builds up to form an internal resistance that affects the accuracy of the output from the electrochemical cell. In the prior art it has been found necessary with these polarographic electrochemical cells to take the cell apart, when it works improperly, and scrub the silver electrode to eliminate the silver chloride coating, thus exposing the bright silver surface for reuse in the cell. Once this is done the cell is reassembled and it will operate satisfactorily. In addition to this physical scrubbing of the silver anode electrode, there is disclosed an electronic means for reactivating the cell by applying a reverse polarity pulse to the cell momentarily. This technique is disclosed in my U.S. Pat. No. 4,077,861. There is still a need in the art, however, for an improved electrochemical cell wherein the cell configuration allows it to be essentially maintenance free. In particular, the polarographic type of electrochemical cell requires that the cell be periodically reactivated and the elimination of this step is an important feature in rendering the cell maintenance free. In the case of sealed electrochemical cells, internal expansion due to both temperature effects and the diffusion of highly mobile background gases into the cell is a continuing problem. There is, therefore, a need to provide a cell that is totally unaffected by the relative diffusion rates of differing background gases. Also, a cell that is constructed without the need for expensive or intricate seals to avoid leaking of the electrolyte is desirable.

SUMMARY OF INVENTION

The present invention provides an improved electrochemical cell of either galvanic or polarographic type that is essentially maintenance free. With respect to the polarographic type of cell, the anode electrode is uniquely defined to have a large surface area available and so that the anode electrode is useful throughout the life of the cell without the need for physically scrubbing the anode electrode or activating it in any way to refurbish the cell during the useful life of the cell. The basic cell is also advantageously defined by the provision of a unique venting structure to minimize the creation of differences in pressures within the cell over time as well as providing the cell with the ability to change background gases that have different permeability rates without any disadvantageous effects on the operation of the cell. The venting structure is also designed to prevent loss of the electrolyte despite the communication of the interior of the cell with the environment. To this end the electrolyte fluid is advantageously, releasably held in a solid-like material that allows the electrolyte to be removed therefrom by capillary action whereby the solid-like material functions as a reservoir for electrolyte without allowing the electrolyte to leak through the venting structure, or otherwise. The structural organization of the electrochemical cell allows it to be advantageously employed as either a galvanic type or polarographic type of cell through the mere substitution of one type of anode electrode for the other.

From the standpoint of the construction of the anode electrode for use in a polarographic electrochemical cell, the present invention provides an anode electrode having a very large surface area that allows it to be utilized for a very long period of time without the need to resort to the prior art techniques for refurbishing it. To this end the anode electrode is provided with the very large porous surface by plating silver on a base material at a relatively high plating rate to produce the porous surface. In arriving at the final porous surface the base material for such an anode electrode, which may be brass, should be initially plated in the conventional fashion with a layer of silver to prevent corrosion of the base material, and then by increasing the normal plating rate to a very high rate, the porous surface will be defined to provide the advantageous structure for the polarographic cell.

From a structural standpoint, the electrochemical cell of the present invention is defined by means of an insulated container having at least a single open end. A cathode electrode means is defined and supported within the container adjacent the open end along with means for defining an anode electrode. The anode electrode means is supported within the container adjacent the open end and spaced adjacent the cathode electrode means. A liquid impermeable, gas permeable membrane means is secured to the open end of the container with the membrane being positioned in intimate contact with the cathode electrode means. The membrane securing means includes an aperture therein for exposing the cathode electrode means to the environmental gases through the membrane. The container also includes means mounted in close association with the cathode electrode means for conveying a fluid electrolyte by capillary action to the cathode electrode means for continuously providing a thin electrolyte film extending between the cathode and the membrane for sensing oxygen or the like diffused through the membrane. The fluid electrolyte is releasably held captive by a solid-like material stored within the container in contact with the electrolyte conveying means, but spaced from the cathode means and the membrane to function as a reservoir of electrolyte. The electrolyte is continuously drawn from the electrolyte holding material by means of capillary action provided by the conveying means in response to the evaporation of water from the electrolyte at the gas permeable membrane to continuously wet the cathode means and the membrane. The electrolyte holding material is further characterized as holding the electrolyte captive to prevent it from flowing away from its storage position independently therefrom except by the conveying means. The container includes means for venting the space between the membrane and the electrolyte holding means to prevent pressure variations therein for maintaining a substantially uniform film of eletrolyte between the membrane and the electrode means without loss of electrolyte to the environment.

The improved structural organization for the electrochemical cell of the present invention can be constructed through the steps of providing an insulated container having an open end and mounting a cathode electrode substantially centrally of the container with the anode electrode exposed at the open end. After the cathode electrode is mounted it is surrounded with a porous element capable of conveying a fluid electrolyte to maintain the cathode electrode wet. An anode electrode is mounted within the container adjacent the cathode electrode on one side thereof. A solid-like material having electrolyte bound thereto, but capable of being released therefrom by the porous conveying element, is positioned within the container so that it will function as an electrolyte reservoir for the cell. The solid-like material is positioned with its top surface spaced a preselected distance from the open end of the container. The exposed surfaces of the porous element and associated electrode surfaces are pre-wet with the fluid electrolyte. The method of construction includes securing a liquid impermeable, gas permeable membrane in intimate contact with the cathode electrode to the container, but exposing the cathode electrode to the environmental gases through the membrane with the membrane and cathode electrode being spaced by a thin film of electrolyte. The construction of the electrochemical cell is completed by venting the space between the top surface of the solid-like material and the closed open end of the container to prevent pressure variations from occurring within the cell. The venting is constructed and defined to communicate the interior of the cell with the environmental gases while preventing the flow of electrolyte therethrough.

The electrochemical cell may include a thermistor element mounted inside the container to provide an electrical means to compensate for temperature effects on the output signal from the cell.

These and other features of the present invention may be more fully appreciated when considered in the light of the following specification and drawings, in which:

BRIEF DESCRIPTION OF THE DRAWINGS

FIG. 1 is a cross-sectional view of the electrochemical cell embodying the present invention;

FIG. 2 is a cross-sectional view taken along the line 2—2 of FIG. 1 with the bottom sealing material substantially removed therefrom to expose the printed circuit board;

FIG. 3 is an enlarged cross-sectional view of the cathode-membrane system of the cell as illustrated in FIG. 1;

FIG. 4 is a simplified schematic circuit diagram of the biasing, sensing circuitry for the electrochemical cell of FIG. 1 when it is operated as a polarographic cell;

FIG. 5 is a cross-sectional view of an embodiment of the electrochemical cell of FIG. 1 adapted to function as a galvanic electrochemical cell in accordance with the present invention; and FIG. 6 is a cross-sectional view taken along the line 6—6 of FIG. 5 with the bottom sealing material substantially removed therefrom to expose the printed circuit board.

DETAILED DESCRIPTION

The present invention can be better appreciated if the basic construction of an electrochemical cell is kept in mind. The basic construction of an electrochemical cell is well known in the art. The electrochemical cell is basically utilized to sense the concentration of oxygen in a gaseous mixture such as air. Oxygen and similar oxidizing gases are sensed in combination with the oxygen that are as strong or stronger than oxygen. This type of electrochemical cell, however, is generally not utilized in measuring the concentration of a particular oxidizing agent wherein other oxidizing agents are in the gases that would interfere with the accuracy of the measurements.

The electrochemical cell for measuring oxygen is constructed and defined with an anode and cathode electrode arranged in an electrolyte solution. A liquid impermeable, gas permeable membrane is secured to the cell to prevent the evaporation of water from the electrolyte and to isolate the medium undergoing measurement from the electrodes and electrolyte. A thin layer of electrolyte is generally provided for wetting the cathode electrode structure. The cathode functions as the oxygen sensing electrode and produces a cathodic reaction upon the diffusion of the gas mixture containing oxygen through the membrane which can be defined as follows:

$$4e^- + O_2 + 2H_2O \rightarrow 4OH^-$$

This equation represents the fact that four electrons are provided at the cathode electrode in the presence of 1 molecule of oxygen (0 valence) plus 2 molecules of water to produce 4 hydroxyl ions. In this process, the valence of oxygen is reduced to its $-2$ state. The cathodic reaction can be driven galvanically by choosing an appropriately active anode material (e.g. lead) or polarographically by the use of a silver anode and a $-0.6$ to $-0.8$ volt polarizing potention (cathode to anode). As a result of the cathodic reaction, the concentration of oxygen can be electrically measured by monitoring the current flow externally between the anode and cathode electrodes. This current flow will be directly proportional to the concentration of oxygen in the gaseous mixture immediately over the gas permeable membrane of the cell.

Now, referring to the drawings in particular, the electrochemical cell 10 basically comprises an anode electrode A, a cathode electrode K, an electrolyte reservoir E, and a liquid impermeable, gas permeable membrane M. The electrochemical cell 10 is constructed with a tubular housing 11 having open ends with the oxygen sensing open end shown as the top end in FIG. 1. The housing 11 is preferably constructed as a nonreactive material such as plastic, and a nylon plastic is suitable for this purpose. The cathode electrode K is arranged adjacent the open, or top, end of the housing 11 and is arranged substantially centrally of the housing 11 with the anode electrode A arranged adjacent one side thereof and the electrolyte solid-like reservoir E arranged in the housing 11 with its top surface spaced a preselected distance from the open end. A cap element 12 secures the membrane M to the housing 11 and closes the open end of the housing 11 when sealed thereto. The cell 10 also includes venting means V positioned above the reservoir E. A Thermistor element T is mounted within the anode electrode A.

It is important to note at the outset that the structural organization of the electrochemical cell 10 will be described as the invention may be embodied for manufacturing a polarographic electrochemical cell 10 but that the cell can be readily modified, as noted hereinabove, by adding a non-polarizable material to the anode structure, such as lead for example, to cause the cell to function galvanically, as is well understood by those skilled in the art of electrochemical cells. No bias voltage need be applied to the electrochemical cell 10 between the anode and cathode electrodes when it is functioning as a galvanically driven cell.

Now, referring to FIGS. 1 and 3, the detailed construction of the cathode electrode K will be examined. The cathode electrode K is constructed by providing a non-porous cathode support element 15. The cathode support element 15 is constructed of a plastic material that has a cylindrical configuration to accept the cathode pin 16K at one end thereof. The cathode pin 16K should be constructed of an inert material so that it doesn't become reduced itself, but only reduces the oxygen. For this purpose the noble metals such as gold, silver, or platinum are satisfactory. Gold has been selected as the preferred material for the cathode pin 16K. The metal pin 16K functioning as the cathode electrode K is mounted in the cathode support element 15 by drilling a hole 15KA in the end of the support 15. The hole 15KA is drilled slightly undersize with respect to the diameter of the pin 16K, about 0.001 to 0.002 inches, to accept the pin 16K when it is pressed into the hole 15KA so that the pin is maintained therein in a stressed condition. This prevents any gap from developing between the sidewall of the hole 15KA provided for the pin 16K and the pin itself to effect the response of the cell 10. The pin 16K is pressed into the cathode support element 15 so that only the upper surface of the pin 16K is exposed to the electrolyte. The pin 16K, however, has a length so that the opposite end thereof is exposed within the support element 15 to allow an electrical contact to be made thereto, as will be explained hereinafter. After this procedure is completed the cathode electrode structure K is provided with a porous electrolyte support 16 surrounding the support element 15. To this end, the porous electrolyte support element 16 is constructed in the form of a hollow cylinder and it is slidably mounted over the cathode support element 15 to extend over substantially the entire length of the cathode support element 15 as illustrated in FIG. 1. The electrolyte support element 16 has a small hole 16A at the end thereof to allow the pin 16K and the immediate area around the pin of the support element 15 to be exposed. To this end the area of the cathode support element 15 immediately around the pin 16K is identified by the reference character 15A in FIGS. 1 and 3. The electrolyte support element 16 may be constructed of a porous polyethylene material so that the porous material 16 will convey the electrolyte from the electrolyte reservoir E to the interface between the cathode electrode K and the membrane M. The electrolyte is conveyed by the porous electrolyte support member 16 by means of capillary action when at least a portion of the member 16 is in contact with the electrolyte reservoir E. To initiate the operation of the cell, the exposed outer surface of the electrolyte supporting element is pre-wet with a liquid electrolyte. This permits the member 16 to function as an electrolyte conveying means in response to the evaporation of water at the cathode-membrane interface.

The assembly of the cathode electrode K is completed by means of the contact pin means housed within the cathode support element 15. To this end, cathode contact pins 17 and 18 are mounted within element 15 and are held therein by means of a compression spring 19. The topmost contact 17 is in physical and electrical engagement with the cathode pin 16K at the bottom side thereof, as illustrated in FIGS. 1 and 3. Each of the contact pins 17 and 18 is provided with a shoulder 17A and 18A, respectively, defined intermediate the ends thereof for seating the ends of the compression spring 19. The compression spring 19 is illustrated as seated between the shoulders 17A and 18A for maintaining a pressure, electrical contact between the pin 17 and the cathode pin 16K and through the spring 19 an electrical circuit is provided to the bottom contact pin 18.

The anode electrode A as defined for polarographic action is a silver pin. The anode electrode A basically comprises a hollow, cylindrical element that may be constructed of brass material as a substrate. The brass material is provided with a layer of silver deposited thereon by conventional electroplating techniques. The hollow construction for the anode electrode A allows a thermistor element T to be mounted therein adjacent the closed end, as illustrated in FIG. 1. The thermistor element T is preferably mounted with a thermal conductive paste 20 to improve the thermal conductivity to the thermistor T so that it more closely tracks the temperature of the environment to which the cell 10 is subjected. The use of a thermistor T in such electrochemical cells is well known in the art. The electrical signal derived from the thermistor is utilized in the sensing circuit of FIG. 5 for electrically compensating for the temperature variations to which the cell is sensitive, as will be explained hereinafter.

The bottom end of the housing 11 is closed off by means of a printed circuit board 21 arranged inwardly of the bottom and then sealed off by means of an epoxy potting compound 22. The printed circuit board 21 has an aperture 21A for receiving the cathode compact pin 18 therein to extend through the board 21. The bottom side of the printed circuit board is provided with a printed circuit element 23 deposited thereon that is in electrical contact with the pin 18 by being soldered thereto. The printed circuit element 23 has a radial circuit path extending from the pin to the outer periphery of the board 21. At this point the board is provided with a cathode terminal pin 25 that is secured thereto and electrically connected to the printed circuit board 21 by soldering. The cathode terminal pin 25 has a length so that it extends outwardly from the bottom side of the board 21 and beyond the bottom end of the housing 11 to function as an external cathode terminal for the cell 10. The anode electrode A is also connected to an anode terminal pin 26 mounted adjacent the outer periphery of the printed circuit board 21 and spaced from the pin 25 to function as an external terminal pin for the anode electrode. The anode terminal pin 26 is connected by means of a solder connection to the printed circuit pattern 27 running in a straight line to a circular printed circuit pattern 27C forming a mechanical electrical connection to the silver anode element A extending through the bottom side of the printed circuit board 21, as illustrated in FIGS. 1 and 2. Internally of the anode electrode A are the insulated lead wires 32L and 33L for the thermistor T which extend outwardly from the open end of the electrode A and spaced outwardly of the printed circuit pattern 27C. These thermistor lead wires 32L and 33L extending out of the open end of the electrode are stripped of their insulation and connected to a pair of thermistor terminal pins 30 and 31. The ends of the lead wires 32L and 33L are soldered to terminal pins 30 and 31 and are thereby mechanically and electrically secured to their respective pins. The thermistor T provides a means, when interconnected as shown in FIG. 4, for compensating for the temperature effects on the cell 10. After all of these electrical connections have been made, the bottom end of the housing 11 is sealed off by means of the epoxy potting compound 22 sealing the end thereof. Accordingly, only the four contact pins, 25, 26, 30, and 31, extend outwardly of the completed housing 11.

The opposite end of the housing 11 is completed by means of a cap member 12 securing the membrane M in position over the electrode pin 16K. The membrane M is constructed of a material that is impermeable to liquids, but permeable to gases. Such membranes are constructed of either a polytetrafluoroethylene plastic material (commercially identified as Teflon) or a polyethylene plastic material. The membrane M functions to minimize the evaporation of water from the electrolyte and to maintain a controlled film of electrolyte between the underside of the membrane and the cathode K. The membrane M is stretched over the open end of the housing 11 over the cathode electrode K and the adjacent sides of the housing 11 to secure this membrane M in position. As illustrated, the cap 12 is provided with a protective element 32 mounted therein, and a spacer 33 mounted to the inside of the element 32. To expose the membrane M to the environment, the cap 12 is provided with a sensing aperture 12S substantially centrally thereof. The inside diameter of the spacer 33 defines the suspension point P, or where the membrane M engages the spacer 33, as illustrated in FIGS. 1 and 3. The spacer 33 is defined to have a thickness so that the pin 16K extends slightly upwardly above the suspension point P. The cathode pin 16K, in one practical embodiment, is displaced upwardly on the order of 0.040 inches above the suspension point P for the membrane M. This secures the membrane M in position once the cap 12 is mounted over the top end of the housing 11. With these elements all in place the cap 12 is sealed to the housing 11 by sealing means, or an epoxy compound, identified by the reference numeral 34, positioned between the bottom end of the cap 12 and the housing 11.

Before the cap 12 is secured in position, as illustrated, the venting element V and the electrolyte reservoir E are positioned. An important feature of the structural organization of the cell 10 is the provision of the venting means V and the specific, unique construction thereof that is particularly advantageous in the configuration of the cell 10 of the present invention. As is recognized in the prior art, different pressures may be created within the cell proper. These internal pressure changes are produced with time, temperature, and exposure to different gases that have different permeability rates. This problem is recognized in the prior art in my prior U.S. Pat. No. 3,767,552, and was solved by providing an expansion chamber 20 by means of the expansion membrane 22 that separated all of the electrolyte from an expansion chamber proper. The expansion chamber 20 was vented to the atmosphere by means of vent holes 36 provided in the cell housing that coupled the expansion chamber 20 with the environment. This structural organization isolated the expansion chamber 20 from the electrolyte proper and so there was no problem of loss of electrolyte through the vent holes 36 in such a prior art structure. Use of such a flexible membrane is of limited application since when the expansion membrane bottoms out against the housing it cannot expand any more, and then the cell operates as if the expansion membrane were not present. Continued expansion will cause the gas permeable membrane utilized for sensing purposes to lift off its cathode structure and produce improper operation of the cell.

The venting element V of the present invention has been constructed and defined so as to prevent any buildup of pressures within the housing 11 that would affect the desired positioning of the membrane M with regard to the cathode electrode K. The venting element V is defined to communicate the interior of the cell 10 with the environment but is also defined so as to prevent any electrolyte from escaping from within the cell through the venting system. The venting element V has been defined so as to prevent the fluid electrolyte from leaving through the venting aperture even when the cell 10 is mounted on its side, due to the holding properties of the holding material used in the reservoir E and the configuration of the vent V. To this end, then, venting element V is provided as a separate element that is secured to one side wall of the housing 11, as illustrated in FIG. 1. The venting element V is provided with a pressure venting aperture 13V of a diameter as small as possible consistent with the ability to produce it. This structure per se effectively defines a capillary that would cause a liquid to be drawn therethrough. To decouple the capillary 13V and to help prevent electrolyte from being drawn therethrough, a relatively large aperture 13C is defined at the inner end of the element V and arranged in communication with the pressure venting aperture 13C. The aperture 13C is defined within the body of the vent element V that extends inwardly of the inside wall of the housing 11 to extend into the space between the membrane M and the top surface of the electrolyte reservoir E. This construction also minimizes the loss of the fluid when the cell 10 is arranged on its side. The relatively large diameter selected for the aperture 13C is to help prevent any unsupported electrolyte or condensed water from being drawn through the capillary aperture 13V by means of capillary action. In this fashion, then, pressure venting will be realized but electrolyte will not be lost from the cell 10, although a very small portion of the water from the electrolyte will be lost by evaporation through the vent and the membrane. It is imporant that the capillary element 13 be constructed in this fashion, rather than having a straight-through capillary aperture in the housing wall to take care of the pressure variations, since that latter construction would allow the escape of liquids that invariably deposit and cling to the inside surfaces of the housing 11.

In addition to the physical definition of the venting element V, the material utilized for the element V is an important consideration in that it must be a non-wetting material. A material that is found to be satisfactory for this purpose is polytetrafluoroethylene. The provision of a non-wetting material for the vent element V helps prevent it from being coated over with internally deposited liquids and thereby minimizes the loss of fluids therethrough.

The electrolyte reservoir E is constructed of a material to releasably hold the fluid electrolyte captive. The electrolyte holding material holds the electrolyte captive to prevent its flowing away from its desired storage position within the housing 11, but allows it to be withdrawn from the holding material by capillary action. The further characteristic of the holding material it that is permits the electrolyte to be withdrawn therefrom by the electrolyte support element 16. Also, the holding material itself should not be withdrawn into the support element. The electrolyte may be a potassium chloride solution that is held in either a gel material, or a very fine porous sponge. A gel that has been utilized for holding the electrolyte to define the electrolyte reservoir E is a commercially available material that is known as Agarose and is normally used in electrophoresis applications. A one-half percent concentration of Agarose is preferably used. The Agarose is originally in solid form and must be mixed with electrolyte, heated up, and dissolved before it is poured into the housing 11 and allowed to solidify.

As a result of the use of the venting means V, the present invention contemplates the provision of the reservoir E terminating in the housing 11 a preselected distance below the membrane M and utilizing in combination therewith the porous electrolyte element 16 for conveying the fluid electrolyte from the reservoir E to the electrode-membrane interface. To permit this to function properly the porous material 16 is pre-wetted with gel-free electrolyte prior to the formation of the electrolyte reservoir E. Accordingly, the electrolyte holding gel E is then placed in the housing so that it fills the housing 11 from above the printed circuit board 21 to a preselected location below the vent V. To this end the relative temperatures of the element 16 and the gel E are important in initially setting up the cell 10 for proper operation. In manufacturing the cell it is important to note that gel is not desired in the porous electrolyte support 16 so that water in the electrolyte can more easily diffuse from the reservoir E through the porous structure 16 as evaporation occurs at the cathode-membrane interface due to sampling zero relative humidity gas mixtures. If the cathode assembly is maintained relatively cold and the gel relatively warm, the gel can then be poured into the container 11 and will set in a couple of minutes. During this interval the gel will not have sufficient time to diffuse significantly into the porous structure of the element 16.

With the above completed structure for the polarographic cell 10 in mind, the sensing circuitry of FIG. 4 can be examined. The sensing circuitry measures the electron flow generated by the cell 10 by means of an amplifier and meter for electrically signalling the oxygen concentration derived from the anode-cathode pins 26, 25. Consistent with the use of the cell 10 as a polarographic electrochemical cell, a negative bias potential must be applied to the cathode electrode K for the cell 10. The bias potential is supplied by a power source, illustrated as a battery, $E_B$ providing a negative 0.7 volts connected to the cathode pin 25. The positive terminal of the source $E_B$ is connected to a reference potential or ground. The anode pin 26 is connected to the negative input terminal of a differential operational amplifier SA which has its positive input terminal connected to ground. The thermistor pins 30 and 31 are connected in a feedback loop from the output terminal of the amplifier SA to the negative terminal of the amplifier. The meter is connected between the output terminal of the amplifier SA and ground.

The temperature changes to which the cell 10 is subjected will cause a change in the output of the meter in accordance therewith. Since the thermistor is also temperature sensitive it will vary the gain of the amplifier SA such that it will compensate for the temperature effects on the cell 10 and provide a corrected output to the meter. The meter can be made to directly provide a visual output indication of the oxygen concentration sensed by the cell 10.

When the cell 10 is to be operated in a galvanic mode the source $E_B$ is not required and the cathode pin 25 is connected directly to the positive terminal of the amplifier SA. In addition, the anode electrode A is modified to be a lead electrode consistent with galvanic operation.

Now referring to FIGS. 5 amd 6 the specific embodiment of the electrochemical cell 10 of FIG. 1 is illustrated as the cell may be modified in accordance with the presently preferred embodiment of the invention for galvanic operation. The electrochemical cell 10' for use as a galvanic cell is modified so as to construct and define the anode electrode A to comprise lead wool. The anode electrode A identified in the previous embodiments is also modified so that it cannot function as the anode electrode but merely as a thermistor probe TP, as illustrated in FIG. 5. It should be recognized at the outset that with the modifications to the anode electrode A for galvanic operation the basic construction of the cell 10' and its operation is as previously described hereinabove and the corresponding elements for the cell 10' that are found in the basic embodiment of FIG. 1 bear the same reference numerals throughout.

The thermistor probe TP is basically the same hollow configuration as the anode electrode A for the embodiment of FIG. 1 with the thermistor T mounted adjacent the upper end thereof and secured in place by the thermal conductive paste 20, but is not connected to the anode pin 26. The thermistor probe TP does not function as an electrode for the cell 10', but merely as a probe for the thermistor T. For the purpose the substrate material for the probe TP is provided with a corrosion protective coating on the outer surfaces thereof and an epoxy coating is satisfactory for this purpose. The lead wires 32L and 33L for the thermistor T are connected to the thermistor terminal pins 30 and 31 on the printed circuit board 21', as in the above described embodiment.

To convert the electrochemical cell 10 for galvanic operation it is necessary to provide a lead electrode to function as the anode electrode and in accordance with the embodiment of FIG. 5 the anode electrode comprises lead wool arranged in a particular relationship with the remaining elements of the cell 10'. In constructing the lead wool anode electrode A preselected amount of lead wool is selected consistent with the desired life for the galvanic cell 10' and is mounted at the bottom of the insulative housing 11' for the cell 10'. Although the housing 11' for the cell is basically the same as the housing 11 as previously described, the bottom end of the cell 11' is closed by means of a partition 40 provided therefor. The partition 40 is provided with an aperture for the cathode pin 18 as well as the aperture for the thermistor probe TP to allow them to extend outwardly of the partition 40. In addition, a connecting lead wire for the lead wool anode electrode A is threaded through an aperture 40 AL to allow the anode electrode to be connected externally of the partition 40 and thereby the housing 11'. The housing 11' is also illustrated with a dependent shroud 41 constructed integrally with the housing proper and is adapted to receive an electrical connector for the four electrical pins that extend from the printed circuit board 21' into the volume surrounded by the shroud 41. Each of the conductive elements that extend through the partition 40 are sealed at the respective apertures therefor and a typical seal is shown for the lead wire 42 as the sealing means 43. The pin 18 and the thermistor probe TP are also similarly illustrated as sealed within the housing 11' above the partition 40 by means of individual sealing elements 43. In making electrical contact with the lead wool anode electrode A it should be recognized that the connecting lead wire for providing the electrical connection should be constructed for a material that is more noble than lead so that the lead anode electrode will oxidize, but not the connecting lead wire. Materials that are more noble than lead are gold, silver, and copper. In the preferred embodiment, the lead wire 42 is selected to be constructed of copper, since it is less expensive and readily available.

The lead wool electrode A is positioned within the insulative housing 11' at the bottom end therein to abut against the partition 40 and is arranged immediately adjacent the porous electrolyte support element 16 and surrounds this element, as illustrated in FIG. 5. In the construction of the anode electrode A a preselected length of copper lead wire 42 is threaded through the aperture 40 AL and is of an extended length so as to be packed intimately in electrical conductive relationship with the lead wool packed into the bottom of the housing 11'. This arrangement assures electrical conductivity between these two elements. The lead wire 42 extends through an aperture 44 provided in the printed circuit board 21' and is secured thereto by means of solder S. The solder S then is provided with a linear conductive circuit path 45 and is connected with the solder surrounding the anode pin 26' extending outwardly of the printed circuit board 21', as in the previous embodiment. Accordingly, the printed circuit board 21' is modified to the extent of the modifications of the anode electrode and the thermistor probe TP for the cell 10' and permits the four pins 25, 26', 30 and 31 to extend into the shroud 41 for the housing 11' and outwardly from the epoxy sealing material 22 securing the printed circuit board to the housing 11'. The connection of the cathode electrode by means of the pin 18 to the cathode pin 25 is the same as previously described and illustrated in FIG. 2. The four pins 25, 26', 30 and 31 are accessible within the shroud 41.

After the lead wool A and its lead wire 42 are positioned within the housing 11' the cell construction is completed as described hereinabove, namely, the electrolyte reservoir E is positioned in intimate contact with the lead wool anode A so as to cause the anode and cathode electrodes to be immersed in the electrolyte stored within the reservoir E. This provides the necessary electrochemical relationship between the anode and cathode electrodes and the electrolyte as in the previous embodiment.

The completed galvanic cell 10' is operated with the four pins connected into the sensing circuit of FIG. 4, as illustrated therein, except that the cathode pin 25 is connected directly to the positive terminal of the sensing amplifier SA. Stated differently, the cathode electrode is connected directly to the positive terminal of the amplifier SA without the need for the potential source EB, as previously described. The thermistor pins 30 and 31 and the anode pin 26' are connected identically as illustrated in FIG. 4.

I claim:

1. An electrochemical cell comprising an insulative container having an open end, means for defining a cathode electrode supported within the container adjacent the open end, means for defining an anode electrode supported within the container adjacent the open end and spaced adjacent the cathode electrode means, means including a liquid impermeable, gas permeable membrane secured to the open end of the container with the membrane being positioned in intimate contact with the cathode electrode means, said means including an aperture for exposing the cathode electrode means to the environmental gases through said membrane, means mounted in close association with the cathode electrode means for conveying a fluid electrolyte to the cathode electrode means for continuously providing a thin electrolyte film extending between the cathode and the membrane for sensing oxygen or the like diffused through the membrane, a fluid electrolyte releasably held captive by a material stored within said container in contact with said latter mentioned means but spaced from the electrode means and the membrane for functioning as a reservoir of electrolyte, said electrolyte being continuously drawn from said electrolyte holding material by said conveying means in response to the evaporation of water from the electrolyte at said cathode membrane interface to continuously keep wet the electrode means and membrane, said electrolyte holding material being further characterized as holding the electrolyte captive to prevent it from flowing away from its storage position independently therefrom except by said conveying means, and means for venting the space between the membrane and the electrolyte holding means to prevent pressure variations therein for maintaining a substantially uniform film of electrolyte between the membrane and the electrode means without loss of electrolyte to the environment.

2. An electrochemical cell as defined in claim 1 wherein the anode electrode means has an outer porous surface.

3. An electrochemical cell as defined in claim 1 wherein the electrode means and membrane are pre-wetted with electrolyte free of holding material.

4. An electrochemical cell as defined in claim 1 wherein the electrode means and membrane are pre-wetted with electrolyte free of holding material.

5. An electrochemical cell for electrically signalling the quantity of gas, such as oxygen, in a gaseous mixture subjected to the cell, comprising an insulative container having at least a single open end, means for defining a cathode element for the electrochemical cell adjacent the open end thereof and extending outwardly from one side thereof to function as an external cathode terminal, means for defining an anode element for the electrochemical cell adjacent the open end thereof and extending outwardly from one side thereof to function as an external anode terminal, the anode element being internally spaced from the cathode element, a cap member having a central aperture for sealing off the open end of the insulative container, a liquid impermeable, gas permeable membrane stretched across the open end of the container in contact with the cathode element, the cap member being secured to the open end of the insulative container with the membrane being positioned in intimate contact with the cathode element, a liquid electrolyte held in a solid-like material stored in the container to immerse the anode element therein and having its top surface spaced a preselected distance below said membrane for defining a chamber therebetween, the solid-like material holding the electrolyte to prevent the flow thereof apart from the material, means constructed and defined with the cathode element and said membrane to continuously convey the liquid electrolyte from said material to the cathode element to provide a thin electrolyte film extending between the cathode and the membrane to wet said elements for causing the anode element to be oxidized in response to the cathodic reduction of oxygen or the like diffused through the membrane, and vent means constructed and defined in the wall of the insulative container a preselected distance above the top surface of said material for communicating said chamber with the environment through said vent means and to minimize the conveyance of the liquids therethrough.

6. An electrochemical cell as defined in claim 5 wherein said vent means is constructed of a non-wetting material.

7. An electrochemical cell as defined in claim 5 wherein said vent means is constructed and defined with a very small aperture on the order of a capillary extending through the outer wall of the insulative container to communicate with the environment at one end and with a relatively large aperture relative to the small aperture having a portion extending into said chamber from the inner wall of the insulative container.

8. An electrochemical cell as defined in claim 7 wherein said vent means is constructed and defined of a nonwetting material.

9. An electrochemical cell as defined in claim 7 wherein said vent means is constructed of a polytetrafluoroethylene material.

10. An electrochemical cell as defined in claim 5 wherein said liquid conveying means comprises a porous material that wets by capillary action and continuously maintains said elements wet in response to the evaporation of the liquid at said membrane.

11. An electrochemical cell as defined in claim 10 wherein said conveying means is constructed of a porous polyethylene.

12. An electrochemical cell as defined in claim 5 including thermistor means mounted within the insulative container adjacent said membrane and having electrical terminals extending outwardly from one side thereof to function as external thermistor terminals.

13. An electrochemical cell as defined in claim 5 wherein the electrode-membrane system is pre-wetted with electrolyte free of holding material.

14. An electrochemical cell as defined in claim 5 wherein the solid-like material is a gel.

15. An electrochemical cell for electrically signalling the quantity of a gas, such as oxygen, in a gaseous mixture subjected to the cell, comprising a tubular, electrically insulative container, a substantially cylindrical, insulative element arranged substantially centrally of the container adjacent one end thereof, a noble metal pin press-fitted into the closed end of the cylindrical, insulative element to be exposed at the closed end and within said cylindrical element to function as a cathode electrode for the cell, a porous cylindrical element mounted over the cylindrical insulative element to overlie same except that it is spaced from said pin at the closed end of the cylindrical insulative element, contact pin means mounted in the cylindrical insulative element in electrical contact with said pin at one end and extending out of said cylindrical element at the opposite end, anode electrode means mounted within said container adjacent said porous cylindrical element and having an end positioned adjacent said one end of the container and providing an electrical contact at the opposite end of the container, a cap member having a central aperture for sealing off said one end of the container, a liquid impermeable, gas permeable membrane stretched across the cathode electrode, the cap member being secured to said one end of the container with the membrane being held in intimate contact with said cathode electrode, means for sealing off the end of the container opposite from said one end with the anode means and said contact pin means being accessible outside of said sealing means, a liquid electrolyte held in a solid-like material stored in the container to immerse the thus defined anode electrode and the porous cylindrical element therein, the top surface of said material being spaced a preselected distance below said membrane for defining a chamber therebetween, said material being characterized as holding the liquid electrolyte to prevent it from independently flowing as a liquid but being separable therefrom, said porous cylindrical element functioning to withdraw the liquid electrolyte from said material by capillary action and to convey it to said cathode electrode to continuously maintain the electrode-membrane system wet, and vent means constructed and defined in the wall of the insulative container and arranged a preselected distance above said material to provide a conduit between the chamber and the environment, said vent means being further characterized to substantially restrict the flow of liquids therethrough while preventing variations in internal pressures within the container.

16. An electrochemical cell as defined in claim 15 wherein said vent means is constructed of a non-wetting material.

17. An electrochemical cell as defined in claim 15 wherein the end of the container opposite from said one end mounts a printed circuit board adjacent said opposite end, the printed circuit board mounting and securing said cathode pin means and said anode electrical means, individual contact pins for the anode and cathode electrodes secured to the board and extending therefrom outside of the container, a printed circuit deposited on the board for individually connecting the cathode electrode pin with said cathode pin means and the anode electrode pin and said anode electrical means, said sealing means comprising potting means for sealing off the container with only the cathode and anode pins extending outwardly therefrom.

18. An electrochemical cell as defined in claim 15 wherein said porous cylindrical element is constructed of a porous polyethylene material and said cylindrical element of a non-porous material.

19. An electrochemical cell as defined in claim 18 wherein said vent means is constructed of a polytetrafluoroethylene material.

20. An electrochemical cell as defined in claim 19 wherein said vent means is constructed with a very small venting aperture on the order of a capillary extending through the outer wall of the container to provide a path from the chamber to the environment and with a relatively large aperture relative to said small aperture communicating with the venting aperture extending into said chamber from the inner wall of the container.

21. A method of constructing an electrochemical cell comprising the steps of providing an insulative container having an open end, mounting a cathode electrode substantially centrally of the container with the cathode electrode exposed at the open end, surrounding the cathode electrode with a porous element capable of conveying a fluid electrolyte to maintain the cathode electrode wet, mounting an anode electrode within the container adjacent the cathode electrode on one side thereof, positioning within said container a solid-like material having an electrolyte bound thereto but capable of being released therefrom by said porous element whereby the solid-like material functions as an electrolyte reservoir for the cell, the solid-like material having its top surface spaced a preselected distance from the open end of the container, pre-wetting the exposed surfaces of the porous element and associated electrodes not exposed to said solid-like material, securing a liquid impermeable, gas permeable membrane in intimate contact with the cathode electrode to the container but exposing the membrane-cathode electrode system to the environmental gases through the membrane, the membrane and cathode electrode being spaced by a thin film of electrolyte, and venting the space between the top surface of said solid-like material and the thus closed open-end of the container to prevent pressure variations from occurring within the cell, the venting being constructed and defined to communicate the interior of the cell with the environmental gases while preventing the flow of electrolyte therethrough.

22. A method of constructing an electrochemical cell as defined in claim 21 wherein said solid-like material is a gel and the step of positioning said material in the container includes the step of solidifying the gel just after positioning it within the container.

23. A method of constructing an electrochemical cell as defined in claim 21 wherein said solid-like material is a fine porous solid material.

24. A method of constructing an electrochemical cell as defined in claim 21 wherein said solid-like material is a fine porous sponge material.

25. An electrochemical cell comprising an insulative container having an open end, means for defining a cathode means supported within the container adjacent the open end, means for defining an anode electrode means supported within the container, means including a liquid impermeable, gas permeable membrane secured to the open end of the container with the membrane being positioned in intimate contact with the cathode electrode means, said means including an aperture for exposing the cathode electrode means to the environmental gases through said membrane, means mounted in close association with the anode and cathode electrode means for holding and conveying a fluid electrolyte to the anode and cathode electrode means and for continuously providing a thin electrolyte film extending between the cathode and the membrane for sensing oxygen or the like diffused through the membrane, a fluid electrolyte releasably held captive by a material stored within said container in contact with said latter mentioned means but spaced from the cathode electrode means and the membrane for functioning as a reservoir of electrolyte, said electrolyte being continuously drawn from said electrolyte holding material by said conveying means in response to the evaporation of water from the electrolyte at said cathode membrane interface to continuously keep wet the electrode means and membrane, said electrolyte holding material being further characterized as holding the electrolyte captive to prevent it from flowing away from its storage position independently therefrom except by said holding and conveying means, and means for venting the space between the membrane and the electrolyte holding and conveying means to prevent pressure variations therein for maintaining a substantially uniform film of electrolyte between the membrane and the electrode means without loss of electrolyte to the environment.

26. An electrochemical cell for electrically signalling the quantity of gas, such as oxygen, in a gaseous mixture subjected to the cell, comprising an insulative container having an open end and a closed end, means for defining a cathode element for the electrochemical cell adjacent the open end thereof and extending outwardly from one side thereof to function as an external cathode terminal, means for defining an anode element for the electrochemical cell and extending outwardly from the closed end thereof to function as an external anode terminal, the anode element being internally spaced from the cathode element, a cap member having a central aperture for sealing off the open end of the insulative container, a liquid impermeable, gas permeable membrane stretched across the open end of the container in contact with the cathode element, the cap member being secured to the open end of the insulative container with the membrane being positioned in intimate contact with the cathode element, a liquid electrolyte held in a solid-like material stored in the container to immerse the anode element therein and having its top surface spaced a preselected distance below said membrane for defining a chamber therebetween, the solid-like material holding the electrolyte to prevent the flow thereof apart from the material, means constructed and defined with the cathode element and said membrane to continuously convey the liquid electrolyte from said material to the cathode element to provide a thin electrolyte film extending between the cathode and the membrane to wet said elements for causing the anode element to be oxidized in response to the cathodic reduction of oxygen or the like diffused through the membrane, and vent means constructed and defined in the wall of the insulative container a preselected distance above the top surface of said material for communicating said chamber with the environment through said vent means and to minimize the conveyance of the liquids therethrough.

27. An electrochemical cell as defined in claim 26 wherein said anode element is constructed and defined as a lead wool electrode.

28. An electrochemical cell as defined in claim 27 wherein said lead wool electrode comprises a preselected quantity of lead wool arranged between the closed end of the insulative container and the lower end of said electrolyte holding solid-like material and surrounding said electrolyte conveying means.

29. An electrochemical cell as defined in claim 28 wherein said lead wool electrode is electrically connected to a lead wire that is constructed of a noble metal that is selected to be more noble than the lead electrode and extends outwardly from the closed end of the container and connected to an external anode terminal.

30. An electrochemical cell as defined in claim 29 wherein said lead wire is a copper lead wire.

31. An electrochemical cell as defined in claim 28 including thermistor means mounted within the insulative container adjacent said membrane and having electrical terminals extending outwardly from one side thereof to function as external thermistor terminals.

32. An electrochemical cell as defined in claim 31 wherein said thermistor means comprises a thermistor probe supported within the container adjacent the open end and spaced adjacent the cathode electrode means.

33. An electrochemical cell as defined in claim 32 wherein said thermistor probe has a corrosion protective plastic coating on the outer surfaces thereof.

34. An electrochemical cell as defined in claim 33 wherein said coating is an epoxy coating.

35. An electrochemical cell as defined in claim 28 wherein the electrode membrane system is pre-wetted with electrolyte free of holding material.

36. An electrochemical cell as defined in claim 28 wherein the solid-like material is a gel.

37. An electrochemical cell for electrically signalling the quantity of a gas, such as oxygen, in a gaseous mixture subjected to the cell, comprising a cylindrical, electrically insulative container having a substantially closed end and an open end, a substantially cylindrical, insulative element arranged substantially centrally of the container adjacent the open end thereof, a noble metal pin press-fitted into the closed end of the cylindrical, insulative element to be exposed at the closed end and within said cylindrical element to function as a cathode electrode for the cell, a porous cylindrical element mounted over the cylindrical insulative element to overlie same except that it is spaced from said pin at the closed end of the cylindrical insulative element, contact pin means mounted in the cylindrical insulative element in electrical contact with said pin at one end and extending out of said cylindrical element at the opposite end, anode electrode means mounted within said container adjacent said porous cylindrical element and positioned adjacent the closed end of the container and providing an electrical contact through the closed end of the container, a cap member having a central aperture for sealing off said open end of the container, a liquid impermeable, gas permeable membrane stretched across the cathode electrode, the cap member being secured to said one end of the container with the membrane being held in intimate contact with said cathode electrode, means for sealing off the open end of the container with the anode means and said contact pin means being accessible outside of said sealing means, a liquid electrolyte held in a solid-like material stored in the container above the thus defined anode electrode and adjacent the porous cylindrical element therein, the top surface of said material being spaced a preselected distance below said membrane for defining a chamber therebetween, said material being characterized as holding the liquid electrolyte to prevent it from independently flowing as a liquid but being separable therefrom, said porous cylindrical element functioning to withdraw the liquid electrolyte from said material by capillary action and to convey it to said cathode electrode to continuously maintain the electrode-membrane system wet, and vent means constructed and defined in the wall of the insulative container and arranged a preselected distance above said material to provide a conduit between the chamber and the environment, said vent means being further characterized to substantially restrict the flow of liquids therethrough while preventing variations in internal pressures within the container.

38. An electrochemical cell as defined in claim 37 wherein said anode electrode means comprises a preselected quantity of lead wool spaced adjacent and immediately below said solid like material and between the inner walls of the container and the outer walls of the porous cylindrical element.

39. A method of constructing an electrochemical cell comprising the steps of providing an insulative container having an open end and a substantially closed end, mounting a cathode electrode substantially centrally of the container with the cathode electrode exposed at the open end, surrounding the cathode electrode with a porous element capable of conveying a fluid electrolyte to maintain the cathode electrode wet, mounting an anode electrode within the container adjacent the closed end of the container, positioning within said container a solid-like material having an electrolyte bound thereto but capable of being released therefrom by said porous element whereby the solid-like material functions as an electrolyte reservoir for the cell, the solid-like material having its top surface spaced a preselected distance from the open end of the container, pre-wetting the exposed surfaces of the porous element and associated electrodes not exposed to said solid-like material, securing a liquid impermeable, gas permeable membrane in intimate contact with the cathode electrode to the container but exposing the membrane-cathode electrode system to the environmental gases through the membrane, the membrane and cathode electrode being spaced by a thin film of electrolyte, and venting the space between the top surface of said solid-like material and the thus closed open end of the container to prevent pressure variations from occurring within the cell, the venting being constructed and defined to communicate the interior of the cell with the environmental gases while preventing the flow of electrolyte therethrough.

40. A method of constructing an electrochemical cell as defined in claim 39 wherein the cell is a galvanic electrochemical cell and said anode electrode is constructed of lead.

41. A method of constructing an electrochemical cell as defined in claim 40 wherein the lead anode electrode is produced by mounting lead wool adjacent the closed end of the container between the inner wall of the container and the outer wall of the porous element and immediately below said solid-like material and with a lead wire extending from the lead wool to the outside of the container.

* * * * *